United States Patent [19]

Samonides

[11] Patent Number: 5,676,785
[45] Date of Patent: Oct. 14, 1997

[54] PRESSURE-SENSITIVE, ADHESIVE-BACKED SUBSTRATES AND METHOD FOR PRODUCING SAME

[75] Inventor: John Samonides, Streamwood, Ill.

[73] Assignee: X-Cal Corporation, Oak Park, Ill.

[21] Appl. No.: 938,252

[22] PCT Filed: Apr. 16, 1991

[86] PCT No.: PCT/US91/02609

§ 371 Date: Oct. 15, 1992

§ 102(e) Date: Oct. 15, 1992

[87] PCT Pub. No.: WO91/16025

PCT Pub. Date: Oct. 31, 1991

Related U.S. Application Data

[63] Continuation of Ser. No. 509,707, Apr. 16, 1990, abandoned.

[51] Int. Cl.$^6$ ................................................. B29C 47/00
[52] U.S. Cl. .......................... 156/244.11; 156/244.16; 156/244.19; 156/244.24; 156/269; 156/270; 156/277; 156/289; 427/208.4
[58] Field of Search ..................... 428/40, 187, 195, 428/201, 203, 204, 352, 354, 355, 343, 480, 481, 483, 511, 516, 447, 448; 283/81; 156/244.11, 244.24, 244.16, 244.19, 269, 270, 289, 230, 240, 241, 277; 427/208.4

[56] References Cited

U.S. PATENT DOCUMENTS

| | | | |
|---|---|---|---|
| 4,068,028 | 1/1978 | Samonides | 428/40 |
| 4,086,379 | 4/1978 | Brown | 428/40 |
| 4,325,770 | 4/1982 | Korpman | 156/230 |
| 4,544,590 | 10/1985 | Egan | 156/240 |
| 4,661,189 | 4/1987 | Voy | 156/248 |
| 4,716,052 | 12/1987 | Waugh | 47/208.4 |
| 4,759,982 | 7/1988 | Jenssen | 428/343 |
| 4,923,919 | 5/1990 | Frazee | 427/208.4 |
| 4,952,650 | 8/1990 | Young | 526/194 |
| 5,089,338 | 2/1992 | Anderson | 428/354 |
| 5,137,764 | 8/1992 | Doyle | 428/44 |
| 5,232,787 | 8/1993 | Gotoh | 428/523 |

*Primary Examiner*—Nasser Ahmad
*Attorney, Agent, or Firm*—Lee, Mann, Smith, McWilliams, Sweeney & Ohlson

[57] ABSTRACT

Pressure-sensitive adhesive-backed substances, such as printed labels, are produced on a release-coated carrier sheet with the printed label indicia sandwiched between the pressure-sensitive adhesive layer and an overlying protecting, preferably transparent, thermoplastic layer. The process for producing the adhesive backed substrate features the extrusion of a water-based, pressure-sensitive acrylic adhesive layer onto the substrate in as near a dry state as possible without heat. Additionally in the label-making process, the overlying thermoplastic layer also may be extruded. The extruded pressure-sensitive water-based acrylic adhesive preferably has a water content of on the order of about 10% by weight, which is just sufficient to permit the extrusion of the adhesive, so that minimal drying is required prior to subsequent processing steps such printing on the adhesive, in the case of the label-making process.

9 Claims, 2 Drawing Sheets

PRESSURE-SENSITIVE, ADHESIVE-BACKED SUBSTRATES AND METHOD FOR PRODUCING SAME

This application is a 35 USC 371 of PCT/US91/02609, filed on Apr. 16, 1991 which is a continuation of Ser. No. 07/509,707 filed Apr. 16, 1990, now abandoned.

This invention relates to pressure-sensitive, adhesive-backed substrates, such as pre-printed labels, having a transparent protective face sheet, and to the process for producing such substrates.

BACKGROUND OF THE INVENTION

Pre-printed, pressure-sensitive, adhesive-backed labels which have a transparent protective face sheet are far superior to paper labels, but heretofore, they have been far more expensive to produce. In U.S. Pat. No. 4,068,028 issued Jan. 10, 1978, there is described a pre-printed pressure-sensitive adhesive-backed label which comprises a transparent face sheet, an adhesive layer adhering to the face sheet, and a silicone coated kraft paper backing. The adhesive layer is imprinted with the label indicia on its outer surface, which is covered by the silicone coated kraft paper backing. In one embodiment, in which both the adhesive and the face sheet are transparent, the printed indicia is clearly visible through both layers. In the other embodiment, where the face sheet is opaque and carries printing on its exterior surface, the printing on the adhesive is visible through a transparent wall, such as a glass bottle, to which the label has been applied. The described process for producing that label requires the initial separate preparation of a composite three-ply sheet consisting of a transparent face sheet, the rear surface of which is coated with a pressure-sensitive adhesive, and a backing sheet which covers the adhesive. The process consists of first delaminating the backing sheet from the composite, then printing the indicia onto the exposed surface of the adhesive, and thereafter relaminating the composite. The result is a very good label in which the indicia may be protected by the transparent face sheet, and is in effect "buried" beneath both the face sheet and adhesive. One problem with that label is that the adhesive must always be transparent if the indicia is to show through the adhesive and the transparent protective face sheet, and of course if the adhesive is clear, then the surface to which the label is affixed will be visible through the face sheet and the transparent adhesive. This type of label is also very expensive, primarily because it requires the separate manufacture of an adhesive-backed substrate prior to the label-making process in which the label is imprinted.

An alternative type of label is the paper label, which does not have the neat finished appearance of the label with the smooth, transparent thermoplastic protective face sheet and does not have any comparable means of protecting the printing. The advantage of the paper label is that it is inexpensive relative to the label with the protective face sheet, and that it may be quickly and easily produced.

It is an object of this invention to provide a pre-printed, pressure-sensitive adhesive-backed label having a transparent protective face sheet which in both quality and appearance is as good as, and in many respects superior to, the previously produced pre-printed labels with the protective transparent face sheet, but which is much less expensive than such prior art labels and rivals the cost of the relatively inexpensive paper labels.

In prior art process adhesives, such as the acrylic adhesives universally used in label and tag making, are normally applied in a liquid state containing 50% or more water or other liquid vehicle. While this simplifies the application of the adhesive to the substrate, the moisture must be subsequently removed to produce the final adhesive-backed product. For example, a pressure-sensitive label contains about 5% moisture by weight, and thus if the adhesive at the time of lamination contains 50% or more moisture by weight, that excess must be driven off in the production of the final adhesive backing before any subsequent printing can occur. Heretofore it was necessary to have the adhesive applied to the substrate by a converter who then supplied the laminated product to the labelmaker for delaminating, printing and cutting into the separate labels. The adhesive simply could not be dried sufficiently to permit printing in the same in-line process with the application of the adhesive because the adhesive could not be dried sufficiently prior to printing and thus would tend to stick to the printing rolls and otherwise result in a poor quality of printing.

It is another object of this invention to provide a unique process for making pressure-sensitive adhesive-backed substrates, such as pre-printed labels having a transparent protective face sheet, which process features the extrusion onto the substrate of the pressure-sensitive adhesive, particularly a water-based acrylic adhesive, with the adhesive having minimal solvent content so that minimal drying is required after the adhesive has been extruded onto the substrate and before subsequent printing can occur. In label making, this process eliminates the necessity of first preparing a laminated product followed by the delamination of that laminated product to effect printing. The process significantly speeds the making of the adhesive-backed substrate and produces labels as good as, and even superior to, prior art processes for making pre-printed labels with protective face sheets. The process is much more economical than prior processes. In face, the process is one which can now occur entirely at the label-making facility, and completely eliminates the converter. In its most preferred aspect, the invention features the extrusion of the water-based, pressure-sensitive acrylic adhesive containing at least 75% solids and preferably about 90% solids.

SUMMARY OF THE INVENTION

In accordance with one embodiment of the invention, the pre-printed pressure-sensitive adhesive-backed labels are formed from a sheet of material which comprises a carrier sheet having one surface coated with a release coating, such as a silicone release coating. The label has a pressure-sensitive adhesive layer, preferably a water-based acrylic adhesive, the first or bottom surface of which is an intimate contact with and releasably adheres to the release coating on the surface of the carrier sheet. On the second or top surface of the pressure-sensitive adhesive layer is printed label indicia, and a thermoplastic protective cover layer covers the printed indicia and is irremovably affixed to the second or top surface of the pressure-sensitive adhesive layer, which is the surface carrying the printed label indicia. At least one of the layers, i.e., the pressure-sensitive adhesive layer or the thermoplastic layer, is transparent, so that upon removal of the carrier sheet, the first or bottom surface of the pressure-sensitive adhesive layer may be adhesively affixed to another surface, such as the surface of a container or the like, and the printed indicia will be visible through the transparent layer. The thermoplastic protective cover layer is preferably the transparent layer, so that the label indicia, which is buried between this layer and the pressure-sensitive adhesive layer, is fully protected and is fully visible after the label has been applied to a smooth supporting surface. The thermoplastic material is preferably polyethylene or polypropylene.

The process for making the pressure-sensitive adhesive-backed substrate comprises preparing a mixture of a pressure-sensitive adhesive and an evaporable liquid vehicle or solvent, preferably water, evaporating the liquid vehicle so that it is present in the mixture only in sufficient quantity to permit extrusion of the mixture, and thereafter extruding the mixture onto the substrate, preferably at about room temperature, but in any event substantially below the melting point of the adhesive. The adhesive mixture may be an emulsion or a dispersion or even a solution of the adhesive and liquid vehicle. The adhesive at the time of extrusion should be within 20 percentage points of the final moisture content of the product by weight, which for a label having a water-based, acrylic adhesive is about 5% moisture by weight. The adhesive at the time of extrusion should have no more than 25% moisture by weight and preferably around 10% moisture by weight.

The process for producing such pre-printed, pressure-sensitive adhesive-backed labels which incorporate the adhesive-backed substrate comprises the step of forming the multi-ply sheet comprising a transparent outer ply, an extruded, pressure-sensitive, water-based, acrylic adhesive central ply which is irremovably attached to said transparent outer ply, and a second outer or carrier ply having a release coated surface removably attached to said adhesive ply; the step of applying a plurality of printed label indicia to the interface of the adhesive central ply and the transparent outer ply during the sheet forming step; and the final step of cutting at least the transparent outer ply and the adhesive central ply into individual labels. In that process, the pressure-sensitive central ply is extruded onto either the carrier ply or the transparent outer ply.

It has been found that the process of producing the labels can be materially speeded up, and a quality label produced, if the pressure-sensitive adhesive is a water-based, acrylic adhesive dispersion which has been thickened and has a minimal water content. This adhesive is extruded onto one of the outer plies. The water content should only be sufficient to permit extrusion. Also in the preferred process, the extruded pressure-sensitive adhesive ply will be further dried by applying a slight amount of heat, preferably followed by cooling by means such as a chill roll or a cooling tunnel. This may be followed by the step of applying a plurality of printed label indicia thereto and then forcing the outer plies and the pressure-sensitive adhesive central ply into intimate contact with one another to form a unitary multi-ply composite sheet. The sheet is then cut or trimmed to form the individual labels. In this process, the extruded adhesive is preferably a water-based, acrylic adhesive containing no more than 20% water and preferably approximately 10% water by weight at the time of extrusion, and the extruded adhesive is further dried to a water content of approximately 5% by weight, which is the normal water content for the finished pressure-sensitive acrylic label. This low water content eliminates the time and energy necessary to dry a comparable water-based adhesive or to heat and then cool a comparable hot-melt pressure-sensitive adhesive.

In the preferred embodiment, not only is the water-based pressure-sensitive adhesive applied by extrusion, but the transparent thermoplastic cover sheet is also applied by extrusion. Thus, the process includes the step of extruding the thermoplastic outer ply onto the pressure-sensitive adhesive central ply, and calendaring the thermoplastic outer ply to a smooth surface finish prior to cutting the sheet to form individual labels. This extrusion of the thermoplastic outer ply is a unique step in the label-making process which materially increases the speed at which the labels may be produced, and thus materially decreases the cost of the labels.

BRIEF DESCRIPTION OF THE DRAWINGS

Reference is now made to the drawings in which.

DETAILED DESCRIPTION OF THE PREFERRED EMBODIMENTS

With reference particularly to FIGS. 1 through 6, in which there is shown schematically a label-forming press of the type which may be used to form the labels and practice the processes of the first embodiment of the invention. While the product formed is a label, and the apparatus and processes described are label-making apparatuses and processes, it will be appreciated that certain aspects of the processes described will have application to the production of a wide variety of other pressure-sensitive adhesive-backed products.

Figure 1:
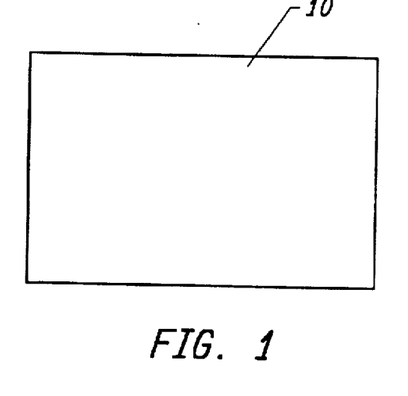
FIG. 1 is a schematic illustration of one embodiment of the label-forming process incorporating the features of the present invention showing the formation of a sheet of labels.
Figure 2:
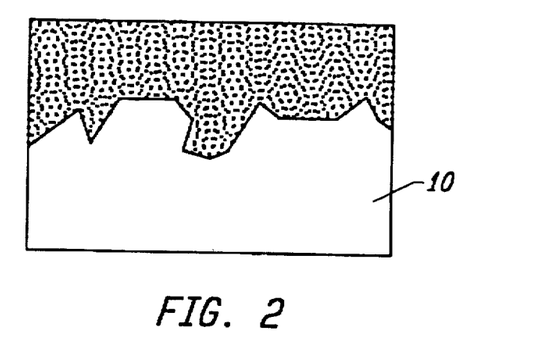
FIG. 2 is an enlarged fragmentary cross-sectional view of the label sheet taken substantially along line 2—2 of FIG. 1.
Figure 3:
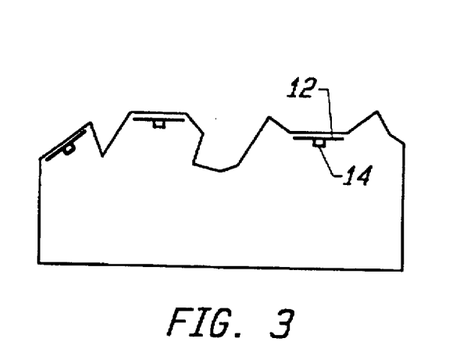
FIG. 3 is an enlarged fragmentary cross-sectional view taken substantially along line 3—3 of FIG. 1.
Figure 4:
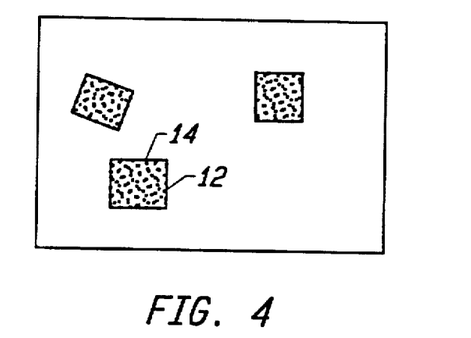
FIG. 4 is an enlarged fragmentary cross-sectional view taken substantially along line 4—4 of FIG. 1.
Figure 5:
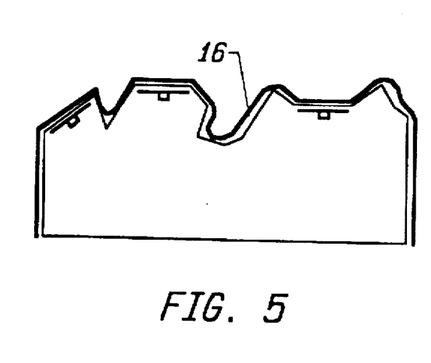
FIG. 5 is an enlarged fragmentary cross-sectional view taken substantially along line 5—5 of FIG. 1.
Figure 6:
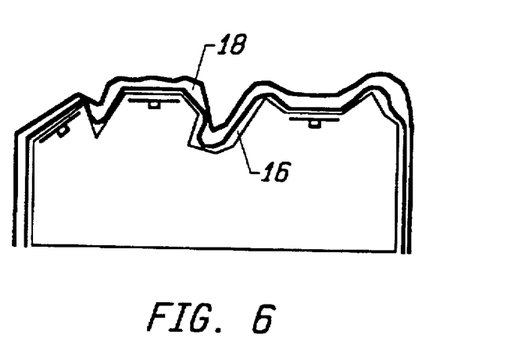
FIG. 6 is an enlarged fragmentary cross-sectional view taken substantially along line 6—6 of FIG. 1.

The press is a standard, well-known color printing press of the type used to print tags and labels. On the left-hand side of the press is a spool or roll 2 containing a supply of a coated carrier sheet 4. The carrier sheet may, for example, consist of a polyester, polypropylene or paper liner or carrier 6, which has been coated on its top surface with a suitable release coating 8 which may be a silicone release coating. The composition of the liner 6 is not important except that it must have a suitable release surface which may be readily separated from the pressure-sensitive adhesive of the label.

The carrier 6 is passed between several guide rolls and then through a web air-guide sensing pickup 10, and across a splicing block 12. The carrier sheet is then guided to an adhesive application station, where it passes over a stabilizing plate 15 and under an adhesive extrusion head 16. At this station, a pressure-sensitive water-based, acrylic adhesive is extruded from an extrusion head 16 which is connected to a screw extruder 18 through a conduit 20. The extruder should be a positive displacement extruder which forces the extrudite out of the extruder by a screw or piston. If necessary, the extrusion head may be connected directly to the extruder 18 and the conduit 20 may be eliminated.

The adhesive is preferably an acrylic adhesive of the type universally used by the tag and label industry to produce pressure-sensitive tags and labels. However, this adhesive differs in one very significant respect—it is almost "dry" as it is being applied to the substrate. The adhesive is a thick, extrudable, water-based, acrylic adhesive which has only sufficient water content to permit extrusion, and it is applied preferably at room temperature with no additional heat. The result is an extruded adhesive layer 22 (See FIG. 3). This adhesive layer 22 is in intimate contact with the silicone release coating 8 on the carrier or liner 6. Even though the adhesive has minimal water content when extruded, i.e., less than 25% by weight and preferably on the order of about 10%, the water must be further reduced to about 5% by weight after extrusion. To accomplish this, the composite is moved through a drying station 23 and then a cooling station 24, and then is guided by suitable guide rolls (which engage only the liner 6 into the first of several printing stations 26).

In the illustrated embodiment, there are seven printing stations which are also designated by the numeral 26. In the first printing station 26, printed label indicia 28 (see FIG. 4) is applied to the adhesive layer 22. Each of the succeeding printing stations 26 may apply a different indicia or different color to the label, and after the printing operation has been completed, the composite sheet consisting of the carrier sheet 6 coated with the silicone release coating 8, and carrying the adhesive layer 22 and the printed label indicia 28 are then guided through a second extrusion station 30, in which the composite sheet passes between a supporting platen 32 and an extrusion head 34. At this extrusion station, hot molten resin, such as polyethylene or polypropylene, is pumped from a reservoir 36 through a conduit 38 to the extrusion head 34, and this resin is extruded as a transparent protective face sheet 40.

From the extrusion station 30, the composite sheet, including the transparent face sheet 40, is passed beneath a calendaring roll 42, which forms a smooth exposed surface on the top of the transparent face sheet. The composite web is then fed downwardly through a chill station 44, and then is fed through a die-cutting station 46, which cuts the sheet into individual labels in the usual and well-known manner. The cutting or trimming die 46 may cut through the face sheet 40 and the adhesive layer 22 without cutting into the silicone-coated carrier or line 6, thus trimming excess material and forming the finished product 48 in which the adhesive-based labels continue to be carried on the continuous uncut carrier sheet. The waste material 50, which has been trimmed or cut away from the release-coated carrier sheet 6, may be wound onto a waste material takeup reel 52. The carrier or liner 6 may be perforated for easy separation of the individual labels thereon, the finished product may then be led down and wound onto a finished product takeup reel 54.

Alternatively, instead of winding the finished product 48 onto the rewind roll 54, the finished product may be sliced into a plurality of discrete labels or sheets of labels 56 in a slicing and stacking station 58. In the illustrated embodiment, there are seven printing stations 26, and it will be appreciated that printing may be accomplished in a single printing station or, if color is desired, the printing may be accomplished in a standard 4-color press, all as is well-known to those skilled in the art.

The process just described produces a protected, subsurface printed label, manufactured in-line, and except for a throwaway liner or carrier 4, employs no other premanufactured product such as a transfer or a protective face sheet. It is much more economical and vastly superior to its counterpart, the paper pressure-sensitive label, and it matches in quality and appearance prior art labels with protective face sheets.

The described process features the extrusion of both the adhesive layer 22 and the transparent face sheet 40. The adhesive is a pressure-sensitive adhesive which preferably is a water-based, acrylic adhesive and may be colorless or tinted. This adhesive is forcibly extruded onto the silicone release coating 8 of the carrier or liner 6. The water-based, acrylic adhesive is preferably of the type which possesses permanent tackiness and is non-yellowing when subject to ultraviolet radiation. One such acrylic adhesive formulation, for example, would be 100 parts acrylate polymer (for stickiness), 20 parts of a tackifier dispersant such as a rosin ester, from about ½% to about 2% by weight humectant such as glycerine or ethylene glycol or hexylene glycol or propylene glycol. The humectant is used for moisture control. From about ½% to about 10% by weight of any well-known UV absorber, such as, for example, a hindered amine of the type sold by Ciba-Geigy under the trademark "Tinuvin" may be employed. From about ¼% to about ½% by weight of a surfactant may be employed for flow control, and a sufficient amount of filler such as calcium carbonate or kaolin clays may be employed to absorb excessive or unwanted moisture in order to achieve an extrudable consistency. The water content is just sufficient to permit extrusion. About 10% by weight has been found acceptable in a water-based acrylic adhesive. If the water content is greater than about 10%, too much drying will be required; if it is less than about 10%, the emulsion will be too thick to properly extrude even with a positive displacement extruder. If desired, any of a number of commercially available acrylic adhesive may be employed, but again the water content must be reduced to about 10% by weight. The result will be a thick, extrudable adhesive similar to that used in the well-known hot-melt adhesive coatings. However, with this water-based acrylic adhesive, no substantial amount of heat is required as the adhesive is being extruded onto the passing silicone-coated carrier liner. The extrusion preferably takes place at room temperature or just slightly above room temperature, i.e., in the range of about 50° F. to about 150° F., which is substantially below the melting point of the adhesive.

The process of extruding the pressure-sensitive adhesive has application to solvent-based adhesives as well, although water-based acrylic adhesives are preferred for the ease of handling and their compatibility with environmental and safety codes. Moreover, as solvent is removed from the system, some solvent-based pressure-sensitive adhesives have a tendency to cross-link, making extrusion difficult. It has been found that water-based acrylic adhesive systems may be brought down to about 10% water by weight and still retain their extrudable characteristics. Thus, water-based, acrylic adhesives are greatly preferred. The word "extrudable" as applied to a pressure-sensitive adhesive and as used herein is intended to mean an adhesive which contains less than 25% by weight liquid vehicle and may be applied using only a positive displacement extruder, such as a screw extruder. In order to extrude such a pressure-sensitive, acrylic adhesive having a water content of in the range of about 10% to about 25% by weight, a screw extruder would generally be required. Such an adhesive could not be easily applied using air pressure, for example. The same requirements prevail for solvent-based adhesives, namely, that the amount of solvent be reduced to a level which will just permit extrusion so that minimal additional drying is required once the adhesive has been extruded onto the substrate.

A slight amount of heat is preferably added to the drying station 23 after the adhesive has been extruded onto the liner to yield the prior tack and to bring the water content of the extruded layer 22 to about 5% by weight. This drying step is followed by cooling, preferably in a cooling station 24 by chill rolls or refrigerated air. This extruded water-based acrylic pressure-sensitive adhesive is considerably more cost-effective than hot-melt adhesives, which may be relatively low cost to purchase but require an enormous amount of energy to melt the pellets for extrusion and to effect the cooling which may be required thereafter, for example, prior to printing. This extruded water-based acrylic pressure-sensitive adhesive is also superior to the well-known wet emulsion adhesive coatings applied at a rather high speed but requiring a tremendous amount of time and energy to dry the vehicle, which generally starts out at between 50 to 60% by weight water. In contrast, the present adhesive starts out (at the extrusion head) with less than 25% water and preferably approximately 10% water and 90% solids by weight. The extruded adhesive is then dried either by air or by adding a slight amount of heat until it has a water content of approximately 5%. The thickness of the adhesive layer after drying is preferably on the order of between 0.0007 and 0.0012 inches, i.e. between 0.7 and 1.2 mils. The extrusion of this water-based acrylic adhesive in a substantially "dry" state enables the printing onto the adhesive in the same run, thereby eliminating the initial preparation of an adhesive-backed substrate prior to the label printing and cutting operations.

The carrier sheet 4 consists of the carrier or liner 6, which, for example, may be a white kraft paper (40-90 lb.) or a 1.5 mil polyester or polypropylene liner, and the silicone release coating which is carried on this liner adheres only lightly to the adhesive layer 22, so that the composite carrier sheet 4 may be readily peeled from the adhesive layer 22 without removing the adhesive from the transparent face sheet 40.

Also produced in-line by means of an extrusion step is the transparent face sheet 40. This face sheet may be formed of a polyester resin or it may be formed of polypropylene or polyethylene. The hot extrusion of polyethylene, polypropylene or polyester is applied in-line on top of the printing, and the composite is then pressed between form rolls which calendar the surface to a very smooth finish and a very close tolerance in thickness. Generally, the face sheet will be one mil to three mils in thickness in a typical label. After the transparent face sheet is calendared, the web is cooled prior to its entry into the die station for die cutting and trimming away the waste.

In FIGS. 7-12, there is illustrated another embodiment of the invention. Though this process is less preferred than the process of FIGS. 1-6, both processes produce a similar product. In this process, a preformed film, such as for example, acrylic, "Mylar" (polyester), polypropylene or polyethylene film, 64 is taken from a roll or spool 62, and passed over and under suitable guide rolls through a web air guide sensing pickup 70, and across a splicing block 72. The film 64 is moved first through one or more printing stations 76, where a mirror-image printed label indicia 78 is applied to what in the finished label will be the "underside" of the film. The film 64 with the printed indicia 78 thereon is then moved to an extrusion station 80 between a supporting platen 82 and an extrusion head 84. In this station the extrusion head receives water-based pressure-sensitive adhesive (of the type previously described) from a conduit 88 leading to a screw extruder (not shown), and casts or extrudes that adhesive as an adhesive layer 90 onto the top surface of the film 64 carrying the printing 78. Thus the printing 78 is sandwiched between the protective film 64 and the substantially "dry" adhesive layer 90. This composite is then moved through a chill box 92 to a laminating station 93. In the laminating station 93 a carrier sheet 96 having a release coating 98 thereon is taken from a supply spool 94, and with the release coated side facing and in registry with the adhesive layer 90 on the film 64, these two are brought together and removably laminated together to form the composite sheet shown in FIG. 11.

Figures 7, 9:
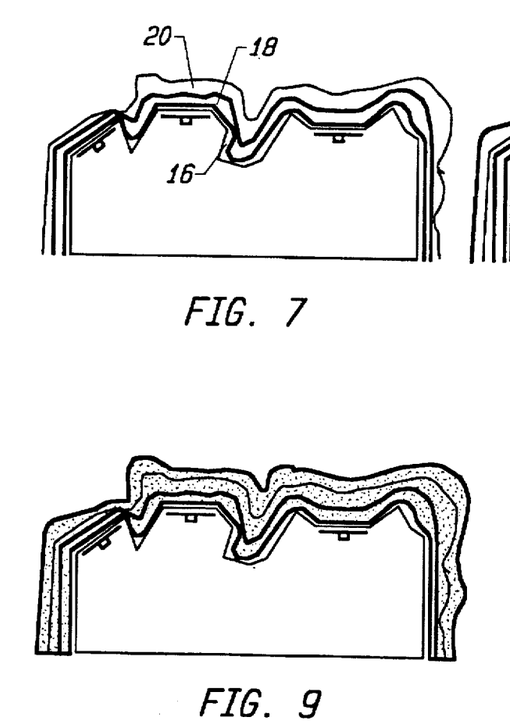
FIG. 7 is a schematic illustration of another embodiment of the label-forming process incorporating features of the present invention.
FIG. 9 is an enlarged fragmentary cross-sectional view taken substantially along 9—9 of FIG. 7.
Figure 7:
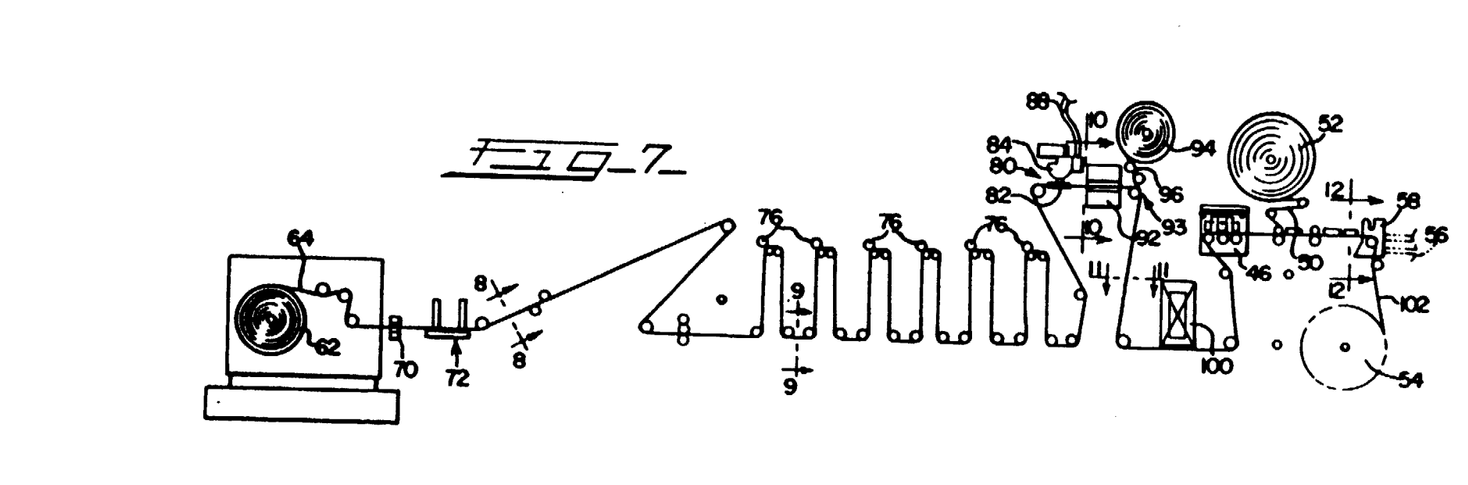
Figures 8, 10:
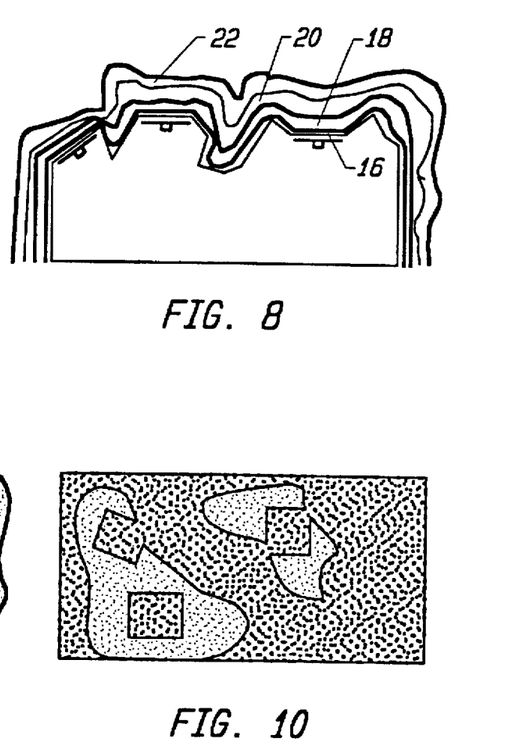
FIG. 8 is an enlarged fragmentary cross-sectional view of a portion of the label sheet taken substantially along line 8—8 of FIG. 7.
FIG. 10 is an enlarged fragmentary cross-sectional view taken substantially along line 10—10 of FIG. 7.
Figure 8:
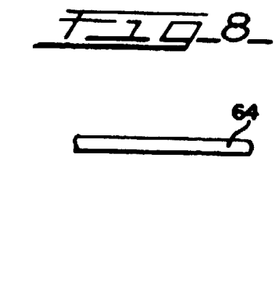
Figure 9:
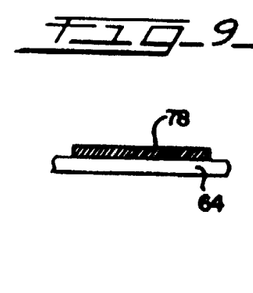
Figure 10:
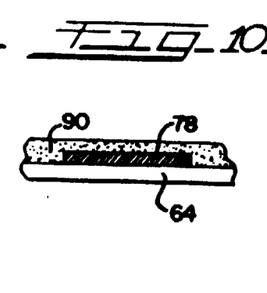
Figure 11:
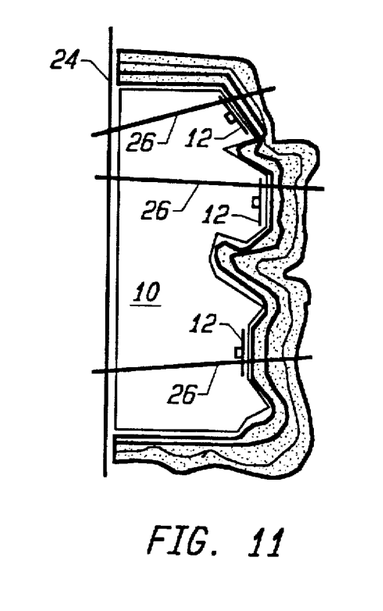
FIG. 11 is an enlarged fragmentary cross-sectional view taken substantially along line 11—11 of FIG. 7.
Figure 12:
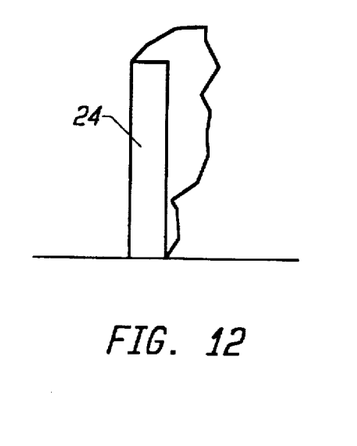
FIG. 12 is an enlarged fragmentary cross-sectional view taken substantially along line 12—12 of FIG. 7.

Thereafter, the laminated sheet is guided through a turn-bar assembly 100 of the type which is described in Pat. No. 4,068,028, which turns the sheet or web through 180° so that the film 64, which had heretofore been at the bottom of the composite, now is at the top. The thus inverted web is then passed to a die-cutting station 46 identical to that described in connection with the previous embodiment, in which the face sheet 64 and adhesive 90 are cut through without cutting into the silicone-coated backing sheet 96, and the waste material 50 is taken up on a takeup reel with the finished product 102 being either wound on a rewind roll 54 or run through a slicing and stacking station 58 where the product is sliced into sheets and stacked.

The foregoing description has been given by way of example of an the various embodiments of the invention. The face sheet 40 and 64 have been described as transparent. It will be appreciated, however, that these films may be opaque so that the label indicia which has been printed on the adhesive layer at the interface with the face sheet is visible through the adhesive and through the underside of the label. This may be desirable where the label is applied to a clear bottle, for example. It is intended that the printed indicia be protected by sandwiching it between the adhesive and the face sheet, and in this connection, it is essential that the face sheet and the adhesive be compatible so that when they are joined, they will not normally be able to be delaminated. In other words, they are irremovably affixed to each other under all normal circumstances. The adhesive, on the other hand, may be an opaque material forming the background for the printed indicia, although in many applications the adhesive will be transparent or translucent.

From the foregoing it may be seen that there has been provided a pre-printed pressure-sensitive label having a thermoplastic protective face sheet and providing a finished appearance which is equal to that of previously pre-printed labels with protective face sheets. The label is superior to, and rivals the cost of, pressure-sensitive adhesive paper labels. The unique process by which these labels are produced eliminates the separate preparation of a laminated product prior to the label-making process, and further eliminates the step of delaminating that product during the label-making process. The process speeds and reduces the cost of the label making, while producing a quality product.

The aspect of the invention which involves the near room-temperature extrusion of a water-based pressure-sensitive acrylic adhesive containing less than 25% water by weight (and preferably about 10%) has application to a wide variety of products, many of which do not involve printing on the adhesive and some of which may not be labels. For example, paper labels can be produced much faster and less expensively utilizing this procedure. Materially reducing the water content of the adhesive reduces the storage space necessary for that adhesive and permits the labels to be produced with less drying required.

As a further example, wallpaper could be produced using an extruded, water-based, pressure-sensitive acrylic adhesive, and again the application of the adhesive would be speeded up and the inventory of adhesive reduced.

It will be understood that various modifications may be made in the example embodiments heretofore set forth, and such modifications and variations will be readily apparent to those skilled in the art. It is intended that the appended claims cover all such modifications as may fall within the true spirit and scope of the invention.

I claim:

1. An in-line process for producing pressure sensitive, adhesive-backed multi-ply labels with one of said plies being a transparent outer ply and another of said plies being a carrier ply having a release coated surface, said process comprising extruding a water based acrylic pressure sensitive adhesive emulsion as a third ply between said other plies, said adhesive containing between about 25% and about 10% water by weight, applying printed label indicia to the interface of said adhesive third ply and the transparent outer ply, cutting at least said transparent outer ply and said adhesive third ply into individual labels and drying the extruded adhesive to a water content approximately 5% by weight.

2. The process of claim 1 wherein the mixture is extruded at a temperature of between 50° F. and about 150° F.

3. The process of claim 1 wherein said sheet-forming step includes the step of extruding the transparent outer ply over the adhesive ply and the printed label indicia, and calendaring said transparent outer ply to form a smooth surface.

4. An in-line process for producing pressure-sensitive labels, said process comprising advancing first and second outer sheets toward one another, the first outer sheet being a transparent face sheet, the second outer sheet being a carrier sheet with a release coating, extruding a pressure-sensitive adhesive emulsion ply containing between about 10% and about 25% water by weight onto one of the sheets, applying printed label indicia at the interface of said adhesive ply and said transparent outer sheet, forcing said outer sheets, said intermediate adhesive ply and said label indicia into intimate contact with one another to form a unitary, multi-ply composite sheet, and cutting at least portions of said composite sheet into individual labels.

5. The process of claim 4 wherein the printed label indicia is applied to the extruded adhesive ply on the surface thereof which will be placed next to said first outer sheet.

6. The process of claim 4 wherein the printed label indicia is applied to said first outer sheet on the inner surface thereof which will be placed next to said extruded adhesive ply.

7. The process of claim 4 wherein said first outer sheet is thermoplastic.

8. The process of claim 4 wherein said pressure-sensitive adhesive ply is extruded onto said second outer sheet and said first outer sheet is advanced toward and brought into contact with said second outer sheet by extruding said first outer sheet onto the surface of said pressure-sensitive adhesive ply after the adhesive ply has been extruded onto the surface of said second outer sheet and after the printed label indicia has been applied to said adhesive ply.

9. An in-line process for producing pressure sensitive, adhesive-backed multi-ply labels with one of said plies being an outer ply and another of said plies being a carrier ply having a release coated surface, said process comprising extruding a water based acrylic pressure sensitive adhesive as a third ply between said other plies, said adhesive being an emulsion, containing a tackifier and between about 25% and about 10% water by weight, applying printed label indicia to said outer ply, cutting a least said outer ply and said adhesive central ply into individual labels and drying the extruded adhesive to a water content of approximately 5% by weight.

* * * * *

UNITED STATES PATENT AND TRADEMARK OFFICE
CERTIFICATE OF CORRECTION

PATENT NO. : 5,676,785  
DATED : Oct. 14, 1997  
INVENTOR(S) : John Samonides

Page 1 of 4

It is certified that error appears in the above-identified patent and that said Letters Patent is hereby corrected as shown below:

The title page should be deleted to appear as per attached.

The drawing sheets consisting of Figs., 1-12 should be deleted to appear as per attached.

Signed and Sealed this

Twenty-fourth Day of March, 1998

Attest:

BRUCE LEHMAN

*Attesting Officer*     *Commissioner of Patents and Trademarks*

United States Patent [19]

Samonides

[11] Patent Number: 5,676,785
[45] Date of Patent: Oct. 14, 1997

[54] PRESSURE-SENSITIVE, ADHESIVE-BACKED SUBSTRATES AND METHOD FOR PRODUCING SAME

[75] Inventor: John Samonides, Streamwood, Ill.

[73] Assignee: X-Cal Corporation, Oak Park, Ill.

[21] Appl. No.: 938,252

[22] PCT Filed: Apr. 16, 1991

[86] PCT No.: PCT/US91/02609

§ 371 Date: Oct. 15, 1992

§ 102(e) Date: Oct. 15, 1992

[87] PCT Pub. No.: WO91/16025

PCT Pub. Date: Oct. 31, 1991

Related U.S. Application Data

[63] Continuation of Ser. No. 509,707, Apr. 16, 1990, abandoned.
[51] Int. Cl.⁶ .................................................. B29C 47/00
[52] U.S. Cl. ................................. 156/244.11; 156/244.16; 156/244.19; 156/244.24; 156/269; 156/270; 156/277; 156/289; 427/208.4
[58] Field of Search ........................... 428/40, 187, 195, 428/201, 203, 204, 352, 354, 355, 343, 480, 481, 483, 511, 516, 447, 448; 283/81; 156/244.11, 244.24, 244.16, 244.19, 269, 270, 289, 230, 240, 241, 277; 427/208.4

[56] References Cited

U.S. PATENT DOCUMENTS

| | | | |
|---|---|---|---|
| 4,068,028 | 1/1978 | Samonides | 428/40 |
| 4,086,379 | 4/1978 | Brown | 428/40 |
| 4,325,770 | 4/1982 | Korpman | 156/230 |
| 4,544,590 | 10/1985 | Egan | 156/240 |
| 4,661,189 | 4/1987 | Voy | 156/248 |
| 4,716,052 | 12/1987 | Waugh | 47/208.4 |
| 4,759,982 | 7/1988 | Jenssen | 428/343 |
| 4,923,919 | 5/1990 | Frazee | 427/208.4 |
| 4,952,650 | 8/1990 | Young | 526/194 |
| 5,089,338 | 2/1992 | Anderson | 428/354 |
| 5,137,764 | 8/1992 | Doyle | 428/44 |
| 5,232,787 | 8/1993 | Gotoh | 428/523 |

*Primary Examiner*—Nasser Ahmad
*Attorney, Agent, or Firm*—Lee, Mann, Smith, McWilliams, Sweeney & Ohlson

[57] ABSTRACT

Pressure-sensitive adhesive-backed substances, such as printed labels, are produced on a release-coated carrier sheet with the printed label indicia sandwiched between the pressure-sensitive adhesive layer and an overlying protecting, preferably transparent, thermoplastic layer. The process for producing the adhesive backed substrate features the extrusion of a water-based, pressure-sensitive acrylic adhesive layer onto the substrate in as near a dry state as possible without heat. Additionally in the label-making process, the overlying thermoplastic layer also may be extruded. The extruded pressure-sensitive water-based acrylic adhesive preferably has a water content of on the order of about 10% by weight, which is just sufficient to permit the extrusion of the adhesive, so that minimal drying is required prior to subsequent processing steps such printing on the adhesive, in the case of the label-making process.

9 Claims, 2 Drawing Sheets